US012121284B2

(12) United States Patent
Galander et al.

(10) Patent No.: US 12,121,284 B2
(45) Date of Patent: Oct. 22, 2024

(54) ELECTROSURGICAL SYSTEM, ELECTROSURGICAL GENERATOR AND ELECTROSURGICAL INSTRUMENT

(71) Applicant: OLYMPUS WINTER & IBE GMBH, Hamburg (DE)

(72) Inventors: Cecilia Galander, Berlin (DE); Veronika Handrick, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 358 days.

(21) Appl. No.: 17/196,421

(22) Filed: Mar. 9, 2021

(65) Prior Publication Data

US 2021/0290293 A1    Sep. 23, 2021

(30) Foreign Application Priority Data

Mar. 18, 2020 (DE) ............... 10 2020 107 439.5

(51) Int. Cl.
*A61B 18/00* (2006.01)
*A61B 18/12* (2006.01)
*A61B 18/14* (2006.01)

(52) U.S. Cl.
CPC .......... *A61B 18/1206* (2013.01); *A61B 18/14* (2013.01); *A61B 2018/00601* (2013.01); *A61B 2018/1412* (2013.01)

(58) Field of Classification Search
CPC ............ A61B 18/1206; A61B 18/14; A61B 2018/00601; A61B 2018/1412
See application file for complete search history.

(56) References Cited

U.S. PATENT DOCUMENTS 5,846,236 A * 12/1998 Lindenmeier ...... A61B 18/1206
606/38
7,476,233 B1 * 1/2009 Wiener .......... A61B 17/320068
606/169

(Continued)

FOREIGN PATENT DOCUMENTS

DE         69534437 T2    6/2006
DE    102013222800 A1    5/2014

(Continued)

OTHER PUBLICATIONS

Dec. 30, 2020 Office Action issued in German Patent Application No. 102020107439.5.

*Primary Examiner* — Joseph A Stoklosa
*Assistant Examiner* — Annie L Shoulders
(74) *Attorney, Agent, or Firm* — Oliff PLC

(57) ABSTRACT

An electrosurgical system is disclosed, including an electrosurgical generator and an electrosurgical instrument which is or can be connected to the electrosurgical generator, wherein the electrosurgical instrument comprises at least a first activation element and a second activation element and the electrosurgical generator is configured to, on actuation of the first activation element, deliver an electrosurgical therapy signal having a first signal shape to the electrosurgical instrument, and, on actuation of the second activation element, deliver an electrosurgical therapy signal having a second signal shape. The system is characterized in that the first signal shape and the second signal shape are identical, and in that the electrosurgical generator is further configured to only perform success monitoring of a tissue effect achieved by the electrosurgical therapy signal on actuation of the first activation element.

10 Claims, 1 Drawing Sheet

(56) References Cited

U.S. PATENT DOCUMENTS

2014/0148803 A1\* 5/2014 Taylor ................ A61B 18/1445
  606/49
2018/0116688 A1\* 5/2018 Akagane ............ A61B 18/1445
2019/0336154 A1\* 11/2019 Batchelor .......... A61B 18/1442

FOREIGN PATENT DOCUMENTS

EP      1157666 B1   9/2005
GB      2509811 A    7/2014

\* cited by examiner

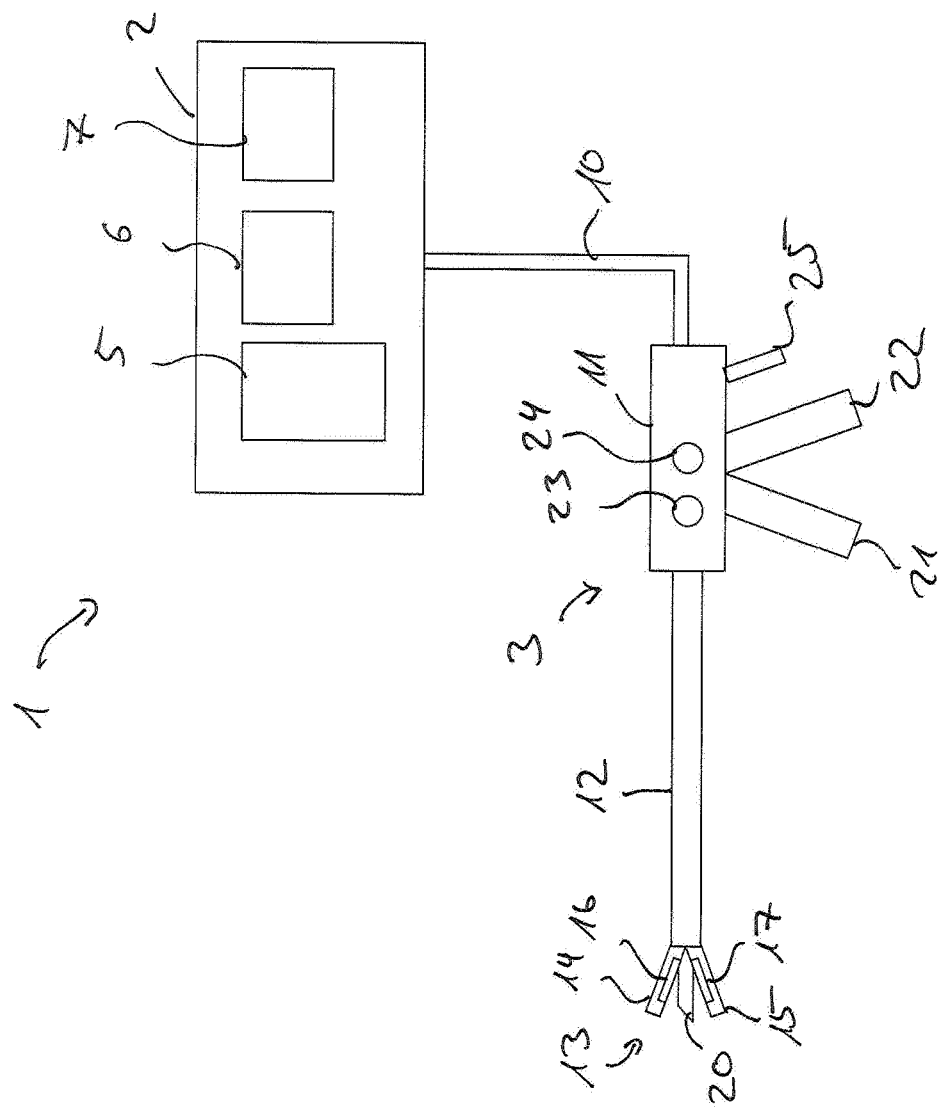

ELECTROSURGICAL SYSTEM, ELECTROSURGICAL GENERATOR AND ELECTROSURGICAL INSTRUMENT

The invention relates to an electrosurgical system comprising an electrosurgical generator and an electrosurgical instrument which is or can be connected to the electrosurgical generator, wherein the electrosurgical instrument comprises at least a first activation element and a second activation element, and the electrosurgical generator is configured to, upon actuation of the first activation element, deliver an electrosurgical therapy signal having a first signal shape to the electrosurgical instrument, and, upon actuation of the second activation element, deliver an electrosurgical therapy signal having a second signal shape. The invention further relates to an electrosurgical generator and an electrosurgical instrument.

Electrosurgical systems are used in modern medicine to perform various procedures. For this purpose, specialized instruments are available for various applications.

Modern electrosurgical generators are capable of determining the progress of electrosurgical procedures by measuring various parameters to verify the achievement of a desired tissue effect, and outputting corresponding signals. Such signals allow an attending physician to determine whether a next step in a procedure may be initiated. If a required tissue effect has not yet been achieved, an electrosurgical generator may output a warning signal.

In more complex procedures, the attending physician may use an instrument that is actually designed for a different procedure to perform minor subsidiary tasks. For example, an instrument designed to seal and cut blood vessels may also be used to stop minor bleeding. This way, time-consuming instrument changes may often be avoided.

In this context, however, the difficulty may arise that on such occasions the success monitoring of the electrosurgical generator remains active unless the attending physician additionally adjusts the generator to a different operating mode. However, this would again delay the procedure.

For example, with activated success monitoring by the generator, the generator may output warning signals when the physician uses the instrument to stop a bleeding and the generator does not detect a complete tissue seal.

To limit the disturbance caused by warning signals in such cases, the volume of the generator's signal sounds is occasionally reduced. However, this impairs the perceptibility of the signal sounds in those situations in which the physician is dependent upon them.

It is therefore an object of the invention to provide an electrosurgical system which is improved with respect to the problems described.

According to a first aspect of the invention, this object is achieved by an electrosurgical system comprising an electrosurgical generator and an electrosurgical instrument which is or can be connected to the electrosurgical generator, wherein the electrosurgical instrument comprises at least a first activation element and a second activation element, and the electrosurgical generator is configured to, upon actuation of the first activation element, deliver an electrosurgical therapy signal having a first signal shape to the electrosurgical instrument, and, upon actuation of the second activation element, deliver an electrosurgical therapy signal having a second signal shape, characterized in that the first signal shape and the second signal shape are identical, and in that the electrosurgical generator is further configured to perform success monitoring of a tissue effect achieved by the electrosurgical therapy signal only upon actuation of the first activation element.

By designing the electrosurgical system according to the invention, a user may without time-consuming instrument changes and without changing the operating mode of the electrosurgical generator, on the one hand, use the success monitoring of the generator for special applications, and, on the other hand, deactivate the success monitoring for smaller intermediate steps. The activation elements may be finger switches on the electrosurgical instrument.

In a further embodiment of an electrosurgical system according to the invention, the electrosurgical generator may be configured to output a success signal when, after actuation of the first activation element, a predefined tissue effect has been achieved. For example, a predefined tissue effect may be a complete and sustained occlusion of a blood vessel or the consistent coagulation of a tissue layer before the vessel or tissue layer is cut by a cutting instrument.

The electrosurgical generator may further be configured to output an error signal when, after actuation of the first activation element, a predetermined tissue effect has not been achieved.

The success signal and/or the error signal may be acoustic, haptic, and/or optical signals. Acoustic signals are preferably confirmation and/or warning sounds. Optical signals may be provided by light emitting elements such as LEDs on the electrosurgical instrument and/or on the generator. Haptic signals may be output, for example, via vibration actuator on the electrosurgical instrument.

The electrosurgical instrument may additionally comprise a cutting element and a third activation element for the activation of the cutting element, and may be configured to allow an activation of the cutting element by the third activation element only after the electrosurgical generator has output the success signal.

Through the respective embodiment of the electrosurgical system, it may be avoided that the cutting element is activated before the tissue effect required for this purpose has safely been achieved. For example, if an attending physician accidentally actuates the second activation element to seal a blood vessel and then attempts to cut the blood vessel by activating the cutting element, this may not be possible because a success signal has not yet been output.

The cutting element may comprise a mechanical cutting blade. Alternatively or additionally, the cutting instrument may comprise an electrosurgical cutting electrode.

According to further aspects of the invention, the above object is achieved by an electrosurgical generator and/or an electrosurgical instrument of an electrosurgical system according to the above embodiments. With respect to the advantages and effects achievable thereby, reference is explicitly made to the discussion above.

The invention will be explained in more detail below with reference to an exemplary embodiment, the embodiment shown in the FIGURE being intended merely to contribute to a better understanding of the invention without limiting it.

The FIGURE shows an electrosurgical system 1 comprising an electrosurgical generator 2 and an electrosurgical instrument 3.

The electrosurgical generator 2 includes a functional assembly 5, a controller 6, and a user interface 7.

The functional assembly 5 is used to generate electrosurgical therapy signals, which may be delivered to the electrosurgical instrument 3 via a connecting cable 10.

The controller 6 monitors the functional assembly 5, and performs other superordinate functions, such as logging operational data and communicating with other medical devices, not shown, via a network, also not shown.

The user interface 7 is used to provide a user with information about the status of the electrosurgical generator 2 and the electrosurgical instrument 3, and to allow input of settings and commands. For this purpose, the user interface 7 may have, for example, a monitor, preferably a touch screen, and a speaker.

Some components of the user interface 7 may be positioned outside of a housing of the generator 2. Thus, not shown optical display elements or haptic and/or acoustic signal transmitters may be arranged directly in the electrosurgical instrument 3 and connected to the rest of the user interface 7 via lines in the connection cable 10.

The electrosurgical instrument 3 comprises a main body 11 with an adjacent elongated shaft 12. A forceps jaw 13 with movable forceps branches 14, 15 is positioned at a distal end of the shaft 12. Electrodes 16, 17 are positioned at the forceps branches 14, 15. A cutting element 20 is positioned between forceps branches 14, 15 and is movable in the direction of the shaft 12. For better clarity, the cutting element 20 is shown in the FIGURE in an extended position. However, the cutting element 20 is generally retracted into the shaft 12 when the forceps branches 14, 15 are open.

For actuation of the forceps jaw 13, handle levers 21, 22 are positioned on the main body of the instrument 3. By closing the handle levers 21, 22, the forceps jaw 13 may be closed, with the forceps branches 14, 15 being moved towards each other. In the course, the electrodes 16, 17 come into contact with tissue not shown, which is compressed between the forceps branches 14, 15.

By means of two activation elements in the form of pushbutton switches 23, 24, the generator 2 may be triggered to provide an electrosurgical therapy signal via the cable 10, which is conducted via not shown leads in the instrument 3 to the electrodes 16, 17, and acts on the tissue gripped between the forceps branches 13, 14. In this manner, for example, a blood vessel may be sealed so that it may subsequently be cut by the cutting element 20.

For actuation of the cutting element 20, a further activation element in the form of a lever 25 is positioned on the main body. Actuation of the lever 25 pushes the cutting element 20 in a distal direction out of the shaft 12 so as to cut tissue gripped between the forceps branches 14, 15.

The cutting element 20 may be merely a mechanical blade, or it may also comprise a cutting electrode. In the latter case, actuation of the lever 25 may also cause the generator 2 to deliver an electrosurgical signal suitable for cutting.

During the delivery of therapy signals, the functional assembly 5 of the generator 2 monitors the progress of these signals and sends corresponding data to the controller 6. The controller 6 is configured to use this data to determine the progress of a tissue effect caused by the therapy signal, and to compare it with predefined target values.

If the generator 2 is activated by actuation of the pushbutton switch 23 to deliver a therapy signal, the controller 6 checks at short intervals whether the progress of the therapy signal indicates complete coagulation or sealing of tissue. As soon as this is the case, the controller 6 causes the user interface 7 to output a success signal, which may consist of a short acoustic signal, a short vibration pulse, and/or the activation of a light source on the instrument, for example a green LED. The physician then knows that the sealing or coagulation is complete, and may cut the tissue by actuating the lever 25.

However, if the physician releases the pushbutton switch 23 before the controller 6 has determined that sealing or coagulation has been successfully completed, a warning signal is output via the user interface 7, which in turn may consist of an acoustic signal, a vibration signal, and/or a light signal. The physician then knows that she must first continue the coagulation or sealing before the tissue may be cut, because otherwise a risk of bleeding may be present.

In some situations, the physician only aims to stop minor bleeding. In order to achieve this, for example, she touches a tissue surface with the lateral edges of the forceps branches 14, 15 so that the electrodes 16, 17 contact the tissue to be treated, and briefly activates the generator to provide a therapy signal. In this case, the controller 6 would typically detect that the therapy signal has been deactivated prematurely and accordingly issue a warning signal, which is, however, not necessary.

For this purpose, the instrument 3 comprises the second pushbutton switch 24. On actuation of the pushbutton switch 24, the generator 2 is also activated to deliver the therapy signal, but the monitoring of the tissue effect by the controller 6 is deactivated. As a result, the output of the warning signal is omitted.

The actual signal shape of the therapy signal is independent of which of the pushbutton switches 23, 24, is actuated. As a result, different signal shape definitions in the generator 2 may be avoided, which simplifies the design of the generator 2.

The pushbutton switches 23, 24 may be connected to the generator 2 via separate lines in the cable 10, so that different circuits are closed when the pushbutton switch 23, 24, is actuated. The pushbutton switches 23, 24 may also be connected to the generator 2 via common lines in the cable 10, so that the actuation closes the same circuit in each case. In this case, however, the pushbutton switches 23, 24 may couple different electronic components into the circuit, such as impedances of different magnitudes, so that the generator 2 is capable, based on the impedance of the closed circuit, of determining which of the two pushbutton switches 23, 24 is actuated.

If the physician of tissue unintentionally actuates the pushbutton switch 24 for a complete sealing or coagulation, and the generator 2 therefore does not perform success monitoring, no warning signal will be generated if the actuation is aborted prematurely. To prevent the physician from nevertheless cutting the tissue, the lever 25 may be equipped with a locking element, not shown, which prevents actuation of the lever 25 until a success signal has been output by the generator 2. The locking element may be actuated electromagnetically, for example, and for this purpose the generator 2 may additionally transmit the success signal to the instrument 3 via the cable 10.

The invention claimed is:

1. An electrosurgical system comprising an electrosurgical generator and an electrosurgical instrument which is or can be connected to the electrosurgical generator, wherein the electrosurgical instrument comprises at least a first activation element and a second activation element, and the electrosurgical generator is configured to
   upon actuation of the first activation element, deliver a first electrosurgical therapy signal having a first signal shape to the electrosurgical instrument, and
   upon actuation of the second activation element, deliver a second electrosurgical therapy signal having a second signal shape,
   wherein the first electrosurgical therapy signal delivered by the electrosurgical generator upon actuation of the first activation element and the second electrosurgical therapy signal delivered by the electrosurgical generator upon actuation of the second activation element are identical, and the first signal shape and the second signal shape are identical, and wherein the electrosurgical generator is further configured to:
perform success monitoring of a tissue effect achieved by the first electrosurgical therapy signal only upon actuation of the first activation element, and
not perform success monitoring of a tissue effect achieved by the second electrosurgical therapy signal upon actuation of the second activation element.

2. The electrosurgical system according to claim 1, wherein the electrosurgical generator is configured to output a success signal when, after actuation of the first activation element, a predefined tissue effect has been achieved.

3. The electrosurgical system according to claim 2, wherein the electrosurgical instrument comprises a cutting element and a third activation element for the activation of the cutting element, and the electrosurgical instrument is configured to allow an activation of the cutting element by the third activation element only after the electrosurgical generator has output the success signal.

4. The electrosurgical system according to claim 3, wherein the cutting element is or comprises a mechanical cutting blade.

5. The electrosurgical system according to claim 3, wherein the cutting element is or comprises an electrosurgical cutting electrode.

6. The electrosurgical system according to claim 3, wherein the electrosurgical instrument is configured to not allow activation of the cutting element by the third activation element if only the tissue effect by the second electrosurgical therapy signal upon actuation of the second activation element has been achieved.

7. The electrosurgical system according to claim 1, wherein the electrosurgical generator is configured to output an error signal when, after actuation of the first activation element, a predefined tissue effect has not been achieved.

8. The electrosurgical system according to claim 1, wherein:
(i) the first activation element and the second activation element are connected to the generator via separate lines so that different circuits are closed upon actuation of the first activation element and upon actuation of the second activation element; or
(ii) the first activation element and the second activation element are connected to the generator via common lines so that actuation of the first activation element and actuation of the second activation element closes the same circuit, and the first activation element and the second activation element couple different electronic components into the circuit.

9. An electrosurgical generator of an electrosurgical system, the electrosurgical generator being configured to be connected to an electrosurgical instrument comprising at least a first activation element and a second activation element, the electrosurgical generator being configured to:
upon actuation of the first activation element, deliver a first electrosurgical therapy signal having a first signal shape to the electrosurgical instrument, and
upon actuation of the second activation element, deliver a second electrosurgical therapy signal having a second signal shape,
wherein the first electrosurgical therapy signal delivered by the electrosurgical generator upon actuation of the first activation element and the second electrosurgical therapy signal delivered by the electrosurgical generator upon actuation of the second activation element are identical, and the first signal shape and the second signal shape are identical, and
wherein the electrosurgical generator is further configured to:
perform success monitoring of a tissue effect achieved by the first electrosurgical therapy signal only upon actuation of the first activation element, and
not perform success monitoring of a tissue effect achieved by the second electrosurgical therapy signal upon actuation of the second activation element.

10. An electrosurgical instrument of an electrosurgical system, the electrosurgical instrument comprising at least a first activation element and a second activation element, wherein the electrosurgical instrument is configured to be connected to an electrosurgical generator of the electrosurgical system, and is further configured to:
upon actuation of the first activation element, receive a first electrosurgical therapy signal having a first signal shape from the electrosurgical generator, and
upon actuation of the second activation element, receive a second electrosurgical therapy signal having a second signal shape,
wherein the first electrosurgical therapy signal received from the electrosurgical generator upon actuation of the first activation element and the second electrosurgical therapy signal received from the electrosurgical generator upon actuation of the second activation element are identical, and the first signal shape and the second signal shape are identical, and
wherein success monitoring of a tissue effect achieved by the first electrosurgical therapy signal is performed only upon actuation of the first activation element, and success monitoring of a tissue effect achieved by the second electrosurgical therapy signal upon actuation of the second activation element is not performed.

* * * * *